United States Patent [19]

Kaplan

[11] 4,430,341

[45] Feb. 7, 1984

[54] WATER SOLUBLE PESTICIDAL QUATERNARY AMMONIUM SALT COMPOUNDS

[75] Inventor: Barbara W. Kaplan, South Charleston, W. Va.

[73] Assignee: Union Carbide Corporation, Danbury, Conn.

[21] Appl. No.: 827,263

[22] Filed: Aug. 24, 1977

[51] Int. Cl.³ .................... A01N 43/48; C07C 125/04
[52] U.S. Cl. .................................. 424/250; 560/134; 560/32; 560/115; 544/400; 544/376; 544/377; 546/335; 546/171; 546/309; 546/269; 546/274; 546/270; 549/51; 549/435; 549/362; 549/462; 424/300; 424/263; 424/244; 424/258; 424/285; 424/282; 424/275; 424/278; 260/239 BF

[58] Field of Search .................. 560/134, 32, 115; 544/400, 376, 377; 546/335, 171, 309, 269, 274, 270; 549/51, 435, 362, 462; 260/346.73, 340.5 R, 239 BF, 340.3; 424/300, 263, 244, 250, 258, 285, 282, 275, 278

[56] References Cited

U.S. PATENT DOCUMENTS 3,404,208  10/1968  Robertson et al. ................. 560/134

FOREIGN PATENT DOCUMENTS 1107411  3/1968  United Kingdom ................ 560/134

*Primary Examiner*—Bernard Helfin
*Attorney, Agent, or Firm*—C. J. Vicari

[57] ABSTRACT

Water soluble quaternary ammonium salt compounds exhibit outstanding insecticidal and miticidal activity coupled with reduced mammalian toxicity and acceptable phytotoxicity.

40 Claims, No Drawings

WATER SOLUBLE PESTICIDAL QUATERNARY AMMONIUM SALT COMPOUNDS

This invention relates to bis-(N-alkyl-N-alkanoyl aryl carbamate) salt compounds which contain two quaternary nitrogen moieties and to their preparation. This invention is also directed to insecticidal and miticidal compositions comprising an acceptable carrier and as the active toxicant an insecticidally or miticidally effective amount of a compound of this invention, as well as to a method of controlling insects and mites by subjecting them to an insecticidally or miticidally effective amount of a compound of this invention.

More particularly, this invention relates to compounds of the formula:

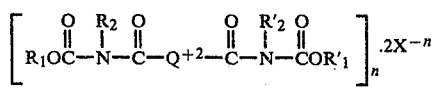

wherein:

n is 1, 2 or 3;

$R_1$ and $R'_1$ are the same or different and are benzofuranyl, benzodixoanyl, naphthyl, benzothienyl, dihydrobenzothienyl, tetrahydronaphthyl, benzodioxolanyl or dihydrobenzofuranyl all of which may be either unsubstituted or substituted with one or more alkyl groups having from 1 to 8 carbon atoms;

$R_2$ and $R'_2$ are the same or different and are alkyl having from 1 to 8 carbon atoms;

X is a monovalent, divalent or trivalent inorganic or organic anion whose total charge equals n;

$Q^{2+}$ is an organic radical which contains two quaternary nitrogen moieties.

As indicated above, X may be any monovalent, divalent or trivalent inorganic or organic anion. Illustrative of the wide range of permissible X groups are:

monovalent inorganic anions, such as chloride, bromide, fluoride, nitrate, iodide and bicarbonate;

divalent inorganic anions, such as carbonate and sulfate;

trivalent inorganic anions such as phosphate;

monovalent organic anions such as acetate propionate, lactate and formate;

divalent organic anions such as succinate, maleate and tartrate.

Trivalent organic anions such as citrate;

arenesulfonates such as p-toluenesulfonate and benzenesulfonate;

alkanesulfonates such as methanesulfonate and ethanesulfonate.

Examples of radicals which $R_1$ and $R'_1$ may represent are 2,3-dihydro-2,2-dimethyl benzofuranyl, 2,3-dihydro-2-methylbenzofuranyl, 2,2-dimethyl-1,3-benzodioxolanyl, or naphthyl.

The alkyl groups which $R_2$ and $R'_2$ represent include methyl, ethyl, isopropyl, n-propyl, hexyl, octyl, isobutyl and the like.

In the preferred embodiments of this invention, $Q^{2+}$ is an organic radical of the formula:

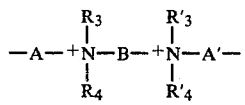

wherein:

A and A' are the same or different and are divalent aliphatic hydrocarbon radical having from 1 to 25 carbon atoms;

B is a divalent aliphatic hydrocarbon radical which may include one divalent oxygen, sulfur, sulfinyl, carbonyloxy, sulfonyl or carbonyl group;

$R_3$, $R'_3$, $R_4$ and $R'_4$ are:

(A) individually either substituted or unsubstituted alkyl, alkoxyalkyl, alkenyl or alkynyl; or (B) when $R_3$ and $R'_3$ are the same or different and are methyl or ethyl, $R_4$ and $R'_4$ are the same or different and are either a substituted or unsubstituted phenyl, naphthyl, cycloalkyl, cycloalkenyl or either a 5 or 6 membered ring structure which may include one or two heteroatoms of oxygen and/or nitrogen; or (C) $R_3$ and $R_4$ and/or $R'_3$ and $R'_4$ together may form either a substituted or unsubstituted alkenylene or alkylene chain having from 2 to 20 carbon atoms, which completes a 3, 4, 5, 6, 7, 8 or 9 membered monocyclic or bicyclic ring structure, said chain may include one or two heteroatoms of oxygen and/or nitrogen; or (D) $R_3$ and $R'_3$ and/or $R_4$ and $R'_4$ together may form either a substituted or unsubstituted alkylene or alkenylene chain having from 2 to 20 carbon atoms which completes a 3, 4, 5, 6, 7, 8 or 9 membered monocyclic, bicyclic or tricyclic ring structure, said chain may include one or two heteroatoms of oxygen and/or nitrogen;

(E) $R_3$, $R'_3$, $R_4$ and $R'_4$ together may form either a substituted or unsubstituted alkylene or alkenylene chain having from 2 to 20 carbon atoms which completes a 3, 4, 5, 6, 7, 8 or 9 membered monocyclic, bicyclic or tricyclic ring structure, said chain may include one or two heteroatoms of oxygen and/or nitrogen;

wherein the permissible substituents that may be substituted on $R_3$, $R'_3$, $R_4$ and $R'_4$ are one or more alkyl, alkoxy, alkanoyloxy, alkoxycarbonyl, cyano, halo, nitro, dialkylamino or alkanoyl groups;

with the proviso that the sum of aliphatic carbon atoms included in $R_3$, $R'_3$, $R_4$ and $R'_4$ may be more than seventy.

Examples of specific radicals which $Q^+$ may represent are:

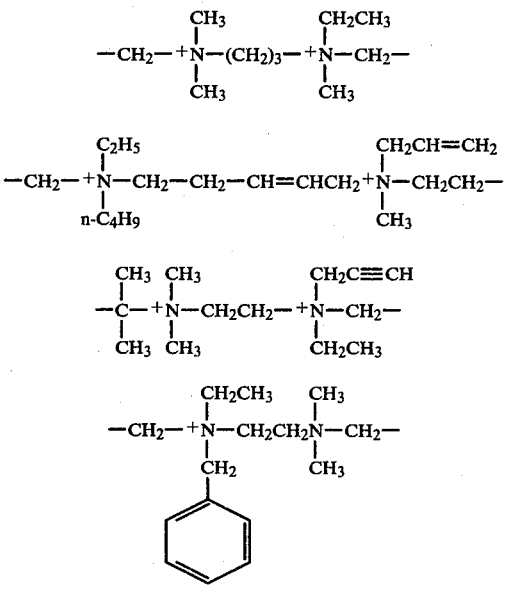

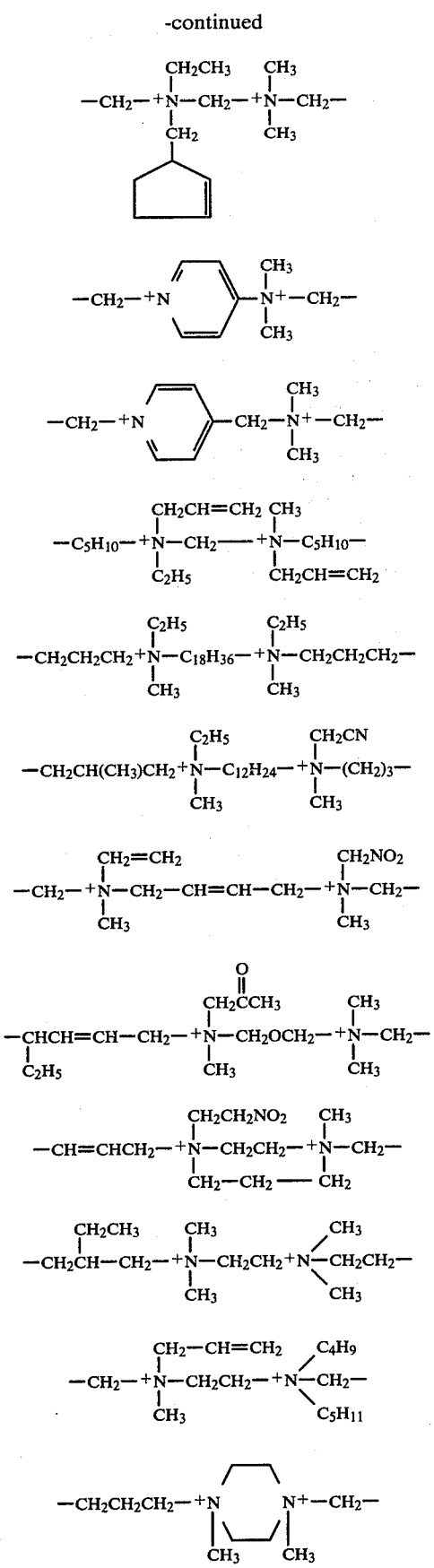
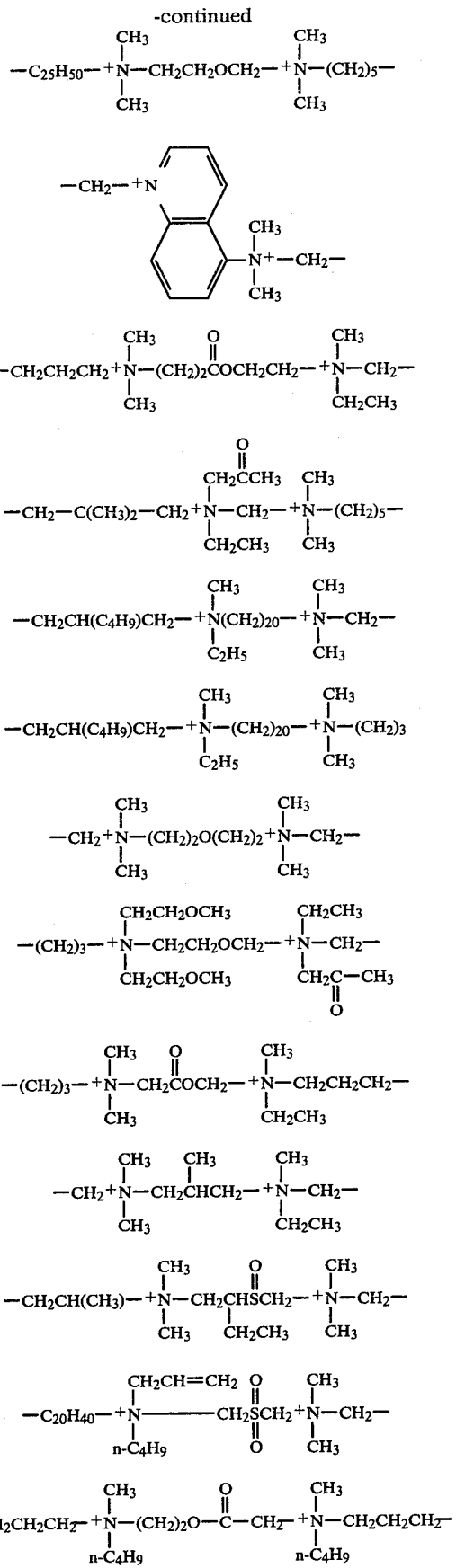

5
-continued
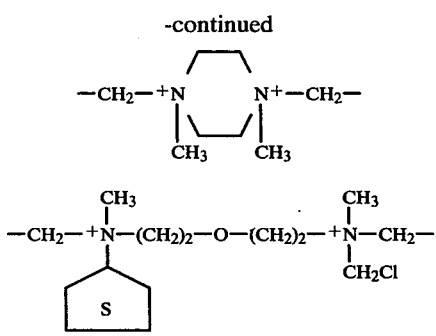
6
-continued
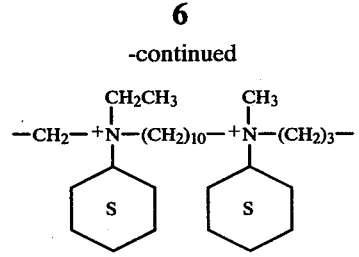
The following compounds are illustrative of the compounds of this invention:
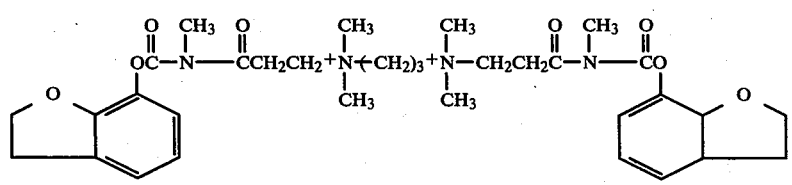
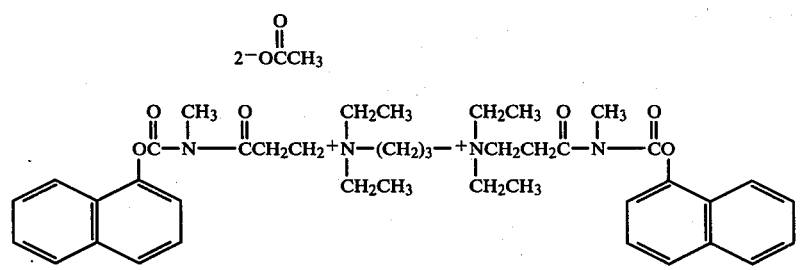
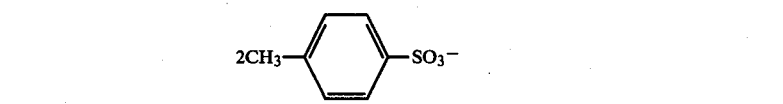
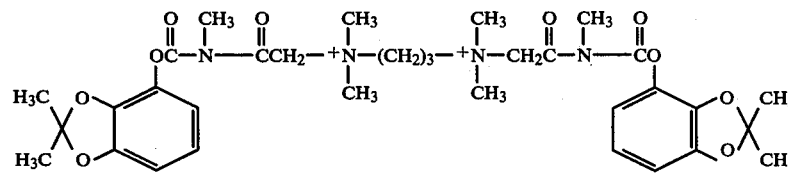
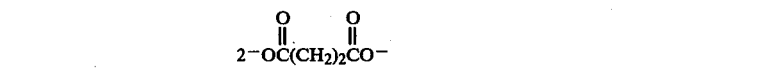
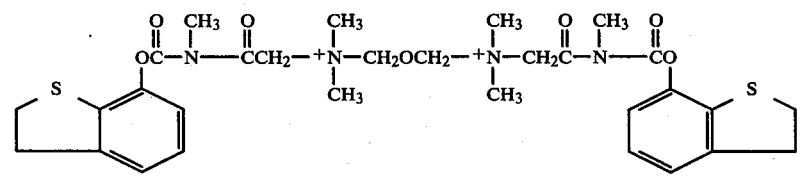
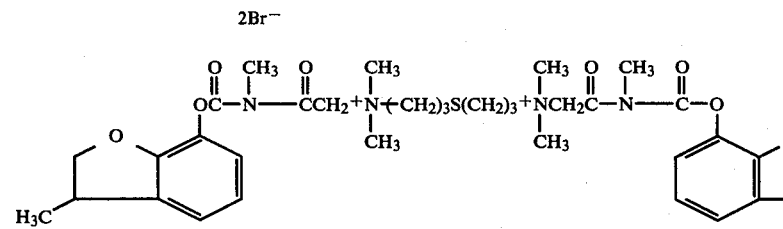

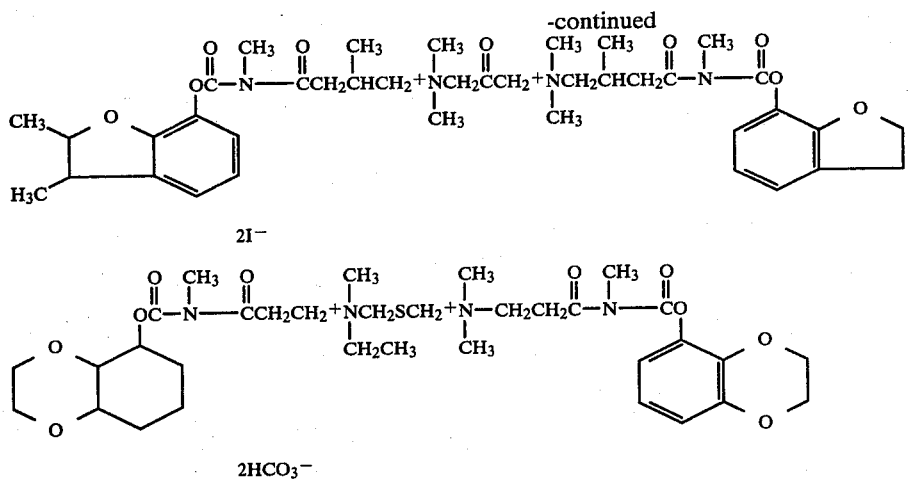

2I⁻

2HCO₃⁻

All of the compounds within the purview of the generic formula set forth above exhibit nematocidal, miticidal and insecticidal activity to a lesser or greater extent. Accordingly, these compounds are extremely useful for the control of insect, nematode and mite pests. Some of these compounds exhibit very high levels of miticidal, nematocidal and insecticidal activity in extremely small dosages while others require larger dosages to be effective. These compounds also exhibit substantially reduced levels of peroral mammalian toxicity as compared to known pesticidal compounds having a comparable spectrum of activity against insect, mite and nematode pests.

The compounds of this invention also exhibit relatively high levels of water solubility as compared to known pesticidally active compounds exhibiting comparable levels of activity. The increased water solubility facilitates the application of the active compounds to the pest. For example, the compounds of this invention which are water soluble can be conveniently and easily used for pest control merely by dissolving the compound directly into water, and then applying the aqueous solution to the pest by some appropriate method, such as spraying. This avoids many of the problems associated with formulations such as crystallization, layer separation, aglomeration and the like.

Preferred, because of their higher levels of insecticidal, nematocidal and miticidal activity and because of their significantly reduced levels of peroral mammalian toxicity and acceptable crop plant phytotoxicity are the compounds of this invention in which:

X is chloride, bromide, nitrate, formate, acetate, p-toluenesulfonate, sulfate, carbonate, methanesulfonate, trifluoromethanesulfonate, phosphate, citrate, propionate, palmitate, laurate, glutarate, valerate, or lactate.

$R_1$ and $R'_1$ are the same or different and are dihydrobenzofuranyl, naphthyl or benzodioxalanyl either unsubstituted or substituted with one or more alkyl substituents having from one to four carbon atoms;

$R_2$ and $R'_2$ are methyl;

A and A' are the same or different and are linear or branched chain alkylene chain having from 1 to 25 carbon atoms; and $R_3$, $R_4$, $R'_3$ and $R'_4$ are as described hereinabove.

B is a linear or branched chain alkylene which may include one divalent oxygen atom.

The compounds of this invention can be prepared by a variety of methods. Two preferred methods are illustrated by the general reaction scheme set forth below in which $R_1$, $R'_1$, $R_2$, $R'_2$, $R_3$, $R_4$, $R'_3$ and $R'_4$ are as described above and X is halide, arenesulfonate or alkanesulfonate except as noted:

METHOD I

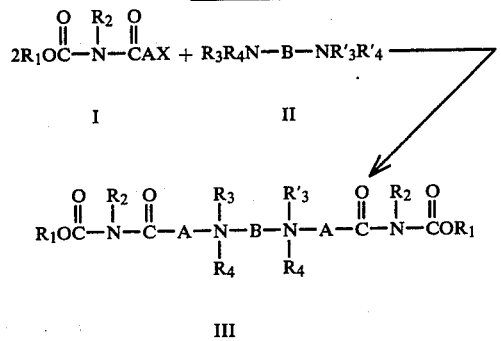

In METHOD I $R_1 = R'_1$, A = A', $R_2 = R'_2$, $R_3 = R'_3$ and $R_4 = R'_4$.

In the procedure illustrated in METHOD I two equivalents of an appropriate N-haloalkanoyl-N-alkyl aryl carbamate compound is reacted with a suitable diamine in an appropriate solvent.

The reaction illustrated in METHOD II is a two-step reaction sequence which can be conducted either in situ or the intermediate, i.e. the product of step A, can be isolated and used as the reactant of Step B at some latter time. In Step A one equivalent of an appropriately substituted N-haloalkanoyl-N-alkyl aryl carbamate reactant, either

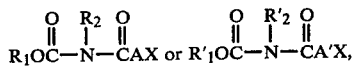

is reacted with one equivalent of the diamine, preferably in an inert solvent to yield the intermediate of Step A is then reacted with a N-haloalkanoyl-N-alkyl aryl carbamate, second equivalent of a reactant,

was used as the reactant in Step A and

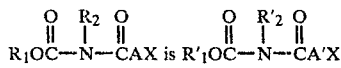

was used as the reactant in Step A. Step B is also preferably conducted in an inert solvent, to yield the desired product.

In general, any organic solvent which is relatively inert to the reactants under the reaction conditions may be employed in the conduct of the reactions of METHOD I and II. Illustrative of the organic solvents which are useful as reaction solvents are saturated and unsaturated aliphatic and aromatic hydrocarbons, e.g. petroleum ether, hexane, cyclohexane, octane, dodecane, naphtha, decalin, kerosene, tetrahydronaphthalene, cyclohexane, benzene, toluene, xylene, naphthalene, ethylbenzene, methylnaphthalene, or the like; ethers such as tetrahydrofuran, tetrahydropyran, diethyl ether dioxane, 1,2-dimethoxybenzene, 1,2-ethoxybenzene, and dialkyl ethers of ethylene glycol, of diethyleneglycol of triethylene glycol, of dipropylene glycol, of butylene glycol, of diethylene glycol, of dipropylene glycol; chlorinated aliphatic hydrocarbons as for example, chloroform, dichloromethane, 1,1-dichloroethane, carbon tetrachloride; ketones, such as acetone or methyl ethyl ketone; and esters such as ethyl acetate.

In general, reaction pressures are not critical. The reaction can be conveniently conducted at either subatmospheric, atmospheric or superatmospheric pressure.

The reaction temperature is not critical and can be varied over a wide range. The process normally can be conducted at a temperature in the range of from about $-30°$ C. and upwards to approximately 180° C. Preferred reaction temperatures are from about 0° C. to about 130° C. At temperatures below $-30°$ C. the rate of reaction becomes markedly slower, while at temperatures above 180° C. product degradation may occur.

Compounds of this invention wherein X is other than halide, alkanesulfonate or arenesulfonate may be conveniently prepared by treating the corresponding quaternary ammonium halide salt compound with the acid of the desired anion or alternatively by passing the solution of the corresponding quaterary ammonium chloride or other salt in water or an organic solvent through an ion exchange resin charged with the appropriate anion. For example N,N,N',N'-Tetramethyl-N,N'-di[(2,3-dihydro-2,2-dimethyl-7-benzofuranyloxy)carboxy-N''-methylaminocarboxymethyl]ethylene-diammonium dinitrite can be conveniently prepared by treating N,N,N',N'-tetramethyl-N,N'-di[(2,3-dihydro-2,2-dimethyl-7-benzofuranyloxy)carboxy-N''-methylaminocarboxymethyl]ethylene-diammonium dichloride with a molar excess of nitric acid in distilled water. By way of a specific illustration of the ion exchange resin method, N,N,N',N'-tetramethyl-N,N'-di[(2,3-dihydro-2,2-dimethyl-7-benzofuranyloxy)carboxy-N''-methylaminocarboxymethyl]ethylene-diammonium diacetate can be conveniently prepared by passing a solution of N,N,N',N'-tetramethyl-N,N'-di[(2,3-dihydro-2,2-dimethyl-7-benzofuranyloxy)carboxy-N''-methylaminocarboxymethyl]ethylene diammonium dichloride in an unreactive solvent, such as water or methylene chloride, through the acetate form of an appropriate resin, as for example, a polystyrene type polymer containing quaternary ammonium acetate groups.

The diamine compounds utilized as reactants in the reactions of Methods I and II are well known compounds that can be either obtained from commercial sources or prepared in accordance with methods well known to those skilled in the synthetic art.

The N-haloalkanoyl-N-alkyl aryl carbamate compounds utilized as reactants in the reactions of Method I can be prepared in accordance with a variety of conventional methods. Three useful methods are illustrated by the reaction schemes set forth below in which $R_1$, $R_2$ and A are as described above and X is chloride and X' is chloride or fluoride and U is iodide, alkanesulfonate arenesulfonate, chloride or bromide.

METHOD III

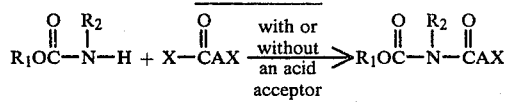

METHOD IV

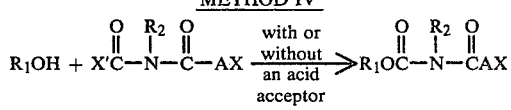

METHOD V

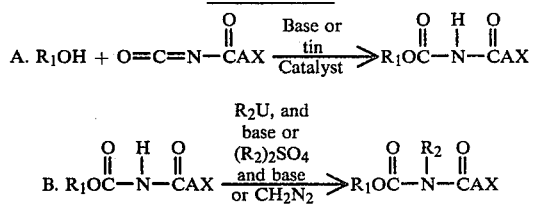

In Method V, $R_2$ is alkyl.

The reactions illustrated in Methods III, IV and V, can be conveniently carried out by contacting equivalent amounts of the reactants and reagents in a suitable nonreactive solvent such as toluene, benzene, methylene chloride, tetrahydrofuran or the like.

Illustrative of useful bases and acid acceptors are aromatic or tertiary amines, sodium bicarbonate, sodium hydroxide, sodium carbonate, potassium hydroxide and the like. Reaction temperatures and pressures are not critical. The reactions can be conducted over a broad temperature and pressure range to yield the desired products.

N-Alkanoyl-N-alkyl aryl carbamate reactants of METHODS I and II in which X is other than chloride, e.g. p-toluenesulfonate, may be conveniently prepared by treating the corresponding chloride compound with salt of the appropriate X group, as for example, sodium p-toluenesulfonate in an appropriate solvent, such as methylene chloride. Such substitutions are well known to those skilled in the art.

The N-alkyl arylcarbamate reactant of Method III can be either obtained from commercial sources or conveniently prepared by reacting an appropriately substituted isocyanate with the corresponding hydroxyl aryl compound in the presence of a catalyst, such as a tertiary amine or a tin compound. The haloalkanoyl halide reactant of METHOD III is a well known compound which can be obtained from commercial sources or prepared by known procedures.

The haloalkanoyl isocyanate reactant of METHOD V is a known compound which can be conveniently prepared by the method disclosed in A. J. Speziale and L. R. Smith, *J. Org. Chem.*, 27, 3742 (1963); 28, 1805 (1963).

The following specific examples are presented to more particularly illustrate the manner in which the compounds of this invention can be prepared.

EXAMPLE I

The preparation of a compound of the formula:

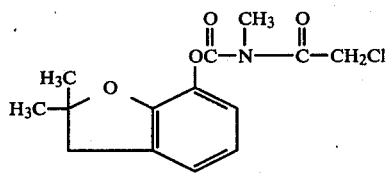

2,3-Dihydro-2,2-dimethyl-7-benzofuranyl N-methylcarbamate (15 g. 0.068 moles) and an excess of chloroacetyl chloride were stirred in refluxing xylene until nuclear magnetic resonance spectroscopy (NMR) showed the reaction to be nearly complete. Partial evaporations and additions of petroleum ether resulted in the crystallization of unreacted starting material, which was removed by filtration. The residue was concentrated to yield 14.54 g (72%) of the compound structurally depicted above as as oil.

Anal. Calc'd for $C_{14}H_{16}ClNO_4$: C, 56.48; H, 5.42; N, 4.70 Found: C, 57.16; H, 5.50; N, 4.46

NMR ($CDCl_3$+TMS): $\delta$=7.26–6.6 (3H); 4.75 (2H); 3.37 (3H); 3.09 (2H); 1.49 (6H)

EXAMPLE II

The preparation of a compound of the formula:

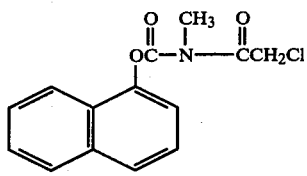

To a 500 ml, one neck round-bottom flask fitted with a magnetic stirrer and a condenser with a nitrogen flow system was added 18.7 g (0.10 m) of 1 naphythyl methyl carbamate, 170 ml of xylene and 16.95 g (0.15 m) of chloroacetyl chloride. The reaction mixture was refluxed for 19 hours and evaporated to a low volume until solids crystalized. The reaction product was collected by filtration and washed with petroleum ether. Successive crops were obtained by partial evaporation of the filtrate and the addition of petroleum ether to yield a total of 13.21 g of the compound structurally depicted above, m.p. 114°–116° C., Anal Cal'd for $C_{14}H_{12}ClNO_3$: C, 60.55; H, 4.36; N, 5.04; Found: C, 60.27; H, 4.02; N, 5.10

NMR ($CDCl_3$+TMS): $\delta$=8.0–7.2 (multiplet, 7H); 4.80 (singlet, 2H); 3,63 (singlet, 3H).

EXAMPLE III

The preparation of a compound of the formula:

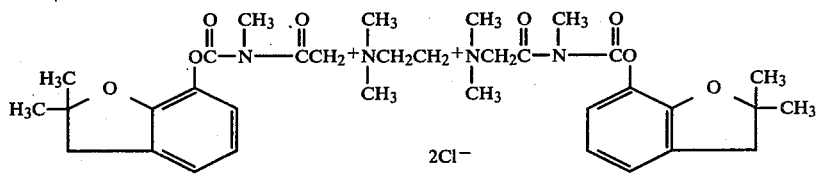

2,3-Dihydro-2,2-dimethyl-7-benzofuranyl N-chloroacetyl-N-methylcarbamate (3.0 g, 0.010 m) and 1.29 g (0.011 m) of N,N,N',N'-tetramethylethylenediamine were stirred in 25 ml of benzene for one hour at 40° C., for 16½ hours at room temperature (25° C.) and for 3 hours at 45°–50° C. After an additional hour at room temperature, the structure of the product depicted above was confirmed by nuclear magnetic resonance spectroscopy (NMR) in $CDCl_3$ with TMS.

EXAMPLE IV

The preparation of a compound of the formula:

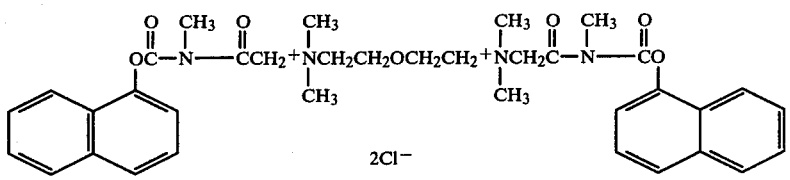

Bis-(dimethylaminoethyl)ether (2.88 g, 0.018 m) was added to a 50° mixture of 5.0 g (0.018 m) of 1-Naphthyl N-Chloroacetyl-N-methylcarbamate in benzene in a 50 ml, three-neck round bottom flask equipped with a thermometer, a stopper, a condenser with a drying tube and a magnetic stirrer. The mixture was held for an additional 1.5 hrs. at 50°–60° C., the mixture was allowed to remain at room temperature for three days. The reaction product crystalized and was collected by filtration. The reaction product was recrystalized from $CH_2Cl_2$ to provide 1.20 g of solid, mp 183°–184° C. with the structure of the compound depicted above. Infrared analysis indicated that the solid contained water. The structure of this compound was confirmed by nuclear magnetic resonance spectroscopy.

Anl. Calc'd for: $C_{36}H_{44}Cl_2N_4O_7$: C, 60.42; H, 6.20; N, 7.83

Infrared Anal (KBr,$Cm^{-1}$): $\lambda$max=1745 (C=O) 1690 (C=O), 1310, 1130

EXAMPLE V

The preparation of a compound of the formula:

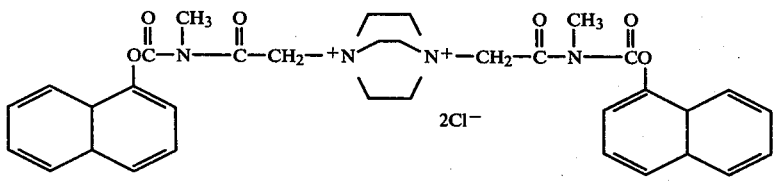

Triethylenediamine (1.01 g, 0.009 m) and 5.0 g (0.018 m) of 1-naphthyl, N-chloroacetyl-N-methyl carbamate and 50 ml of benzene were charged into a four-neck round-bottom flask equipped with a thermometer a magnetic stirrer, two stoppers and a condenser with a drying tube. The reaction mixture was heated at 60° C. for two hours. The reaction product crystalized out and was collected by filtration. The reaction product was washed with hot benzene and dried to yield 4.62 grams of white solids.

The structure depicted above was confirmed by Nuclear Magnetic Resonance Spectroscopy.

EXAMPLE VI

The preparation of a compound of the formula:

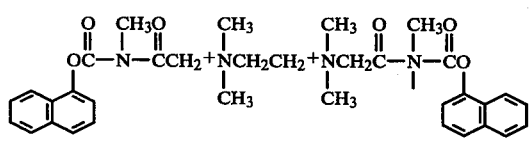

To a solution of 80 g (9.02 gm) of N-chloroacetyl-N-methyl carbamate in 25 ml of benzene was added in a dropwise fashion a solution of 3.68 g (0.032 m) of N,N,N',N'-tetramethylethylenediamine in 25 ml of benzene. During the addition the temperature was held at 50° C. The reaction mixture was stirred at 60° C. for three hours. The reaction product crystalized out and was collected by filtration. The reaction product was recrystalized from $CH_2Cl_2$-benzene to yield a solid whose structure (above) was confirmed by Nuclear Magnetic Resonance Spectroscopy.

EXAMPLE VII

EVALUATION OF INSECTICIDAL AND MITICIDAL ACTIVITY

The compound of EXAMPLE IV was evaluated to determine its pesticidal activity against mites and certain insects, including an aphid, a caterpillar, a beetle and a fly.

Suspensions of the test compound was prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 of milliliters of a suspension containing the compound in finely divided form. The thus-prepared stock suspension contained 0.5 percent by weight of test compound. The test concentrations in parts per million by weight employed in the tests described hereinbelow were obtained by appropriate dilutions of the stock suspension with water. The test procedures were as follows.

Bean Aphid Foliage Spray Test

Adults and nymphal stages of the bean aphid (*Aphis fabae* Scop.) reared on potted dwarf nasturtium plants at 65°–70° F. and 50–70 percent relative humidity, constituted the test insects. For testing purposes, the number of aphids per pot was standardized to 100–150 by trimming plants containing excess aphids.

The test compound was formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Test

Larvae of the southern armyworm (*Prodenia Eridania*, (Cram.), reared on Tendergreen bean plants at a temperature of 80±5° F. and relative humidity of 50±5 percent, constituted the test insects.

The test compound was formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig. air pressure.

This application which lasted 25 seconds was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis, Muls.*) reared on Tendergreen bean plants at a temperature of 80±5° and 50±5 percent relative humidity, were the test insects.

The test compound was formulated by diluting the stock suspension with water to give a suspension containing 500 parts of test compound per million parts of final formulation. Potted Tendergreen bean plants of standard height and age were placed on a revolving turn-table and sprayed with 100-110 milliliters of test compound formulation by use of a DeVilbiss spray gun set at 10 psig air pressure. This application, which lasted 25 seconds was sufficient to wet plants to run-off. As a control, 100-110 milliliters of a water-acetone-emulsifier solution containing no test compound were also sprayed on infested plants. When dry, the paired leaves were separated and each eas placed in a 9 centimeter Petri dish lined with moistened filter paper. Five randomly selected larvae were introduced into each dish, and the dishes were closed. The closed dishes were labeled and held at a temperature of 80±5° F. for three days. Although the larvae could easily consume the leaf within 24 to 48 hours, no more food was added. Larvae which were unable to move the length of the body, even more stimulation, were considered dead.

Fly Bait Test

Four to six day old adult house flies (*Musca domestica, L.*) reared according to the specifications of the Chemical Specialties Manufacturing Association (Blue Book, McNair-Dorland Co., N.Y., 1954; pages 243-244, 261) under controlled conditions of 80±° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compound was formulated by diluting the stock suspension with a 10 percent (by weight) sugar solution to give a suspension containing 500 parts of test compound per million parts of final formulation, by weight. Ten milliliters of the test formulation were added to a souffle cup containing a one inch square of an absorbent cotton pad. This bait cup was introduced and centered on the blotting paper under the food strainer prior to admitting the anesthetized flies. The caged flies were allowed to feed on the bait for twenty four hours, at a temperature of 80±5° F. and the relative humidity of 50±5 percent. Flies which showed no sign of movement on prodding were considered dead.

Mite Foliage Spray Test

Adults and nymphal stages of the two-spotted mite (*Tetranychus urticae Koch*), reared on Tendergreen bean plants at 80±5 percent relative humidity, were the test organisms. Infested leaves from a stock culture were placed on the primary leaves of two bean plants six to eight inches in height, growing in a two- and-a-half inch clay pot. 150-200 mites, a sufficient number for testing, transferred from the excised leaves to the fresh plants in a period of twenty-four hours. Following the twenty-four transfer period, the excised leaves were removed from the infested plants. The test compound was formulated by diluting the stock suspension with water to give a suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted for 25 seconds was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80± percent relative humidity for six days, after which a mortality count of motile forms was made. Miscroscopic examination for motile forms was made on the leaves of the test plants. Any individual which was capable of locomotion upon prodding, was considered living.

In these tests the pesticidal activity of the compounds against aphid, mite, Southern Armyworm, Mexican Bean Beetle, and house fly was rated as follows:

A=Excellent control
B=Partial control
C=No control

PHYTOTOXICITY TEST

Experiments were also conducted to determine the phytotoxicity of a representative composition with respect to healthy fresh plants. A solution of the compound prepared as described above to provide a concentration of 2500 parts per million of the test compound. The test plants were sprayed in accordance with the procedure described above for the Mite Foliage Spray Test so as to deliver approximately 100 milliliters of test solution to the leaves of each plant tested. The sprayed plants and controls were set aside for approximately one hour to allow the solutions to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

The results of these experiments are summarized and set forth in Table I below.

TABLE I

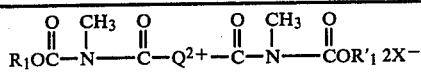

BIOLOGICAL ACTIVITY AND WATER SOLUBILITY

| | % Water Solu- | BIOLOGICAL ACTIVITY Insecticidal and Miticidal So. Mexican |
|---|---|---|

TABLE I-continued $$R_1OC(=O)-N(CH_3)-C(=O)-Q^{2+}-C(=O)-N(CH_3)-COR'_1 \ 2X^-$$

BIOLOGICAL ACTIVITY AND WATER SOLUBILITY

| $R_1$ and $R'_1$ | $Q^{2+}$ | X | % Water Solubility 25° C. | Aphid | Mite | Army Worm | Bean Beetle | House Fly |
|---|---|---|---|---|---|---|---|---|
| 1-naphthyl | $-CH_2-{}^+N(CH_3)_2-CH_2CH_2OCH_2CH_2-{}^+N(CH_3)_2-CH_2-$ | Cl$^-$ | 20 | B | C | A | A | A |

| $R_1$ and $R'_1$ | $Q^{2+}$ | X | % Water Solubility 25° C. | Herbicidal Bean | Cot. | Tom. | Cot. | Soybean |
|---|---|---|---|---|---|---|---|---|
| 1-naphthyl | $-CH_2-{}^+N(CH_3)_2-CH_2CH_2OCH_2CH_2-{}^+N(CH_3)_2-CH_2-$ | Cl$^-$ | 20 | 2 | 1 | 1 | 2 | 2 |

The data in TABLE I clearly illustrates the broad spectrum high level pesticidal activity and the significant water solubility exhibited by the compounds of this invention. In addition, the data shows the low levels of phtotoxicity exhibited by the compounds of this invention. It should be understood that the pests evaluated are representative of a wider variety of pest which can be controlled by the compounds of this invention.

The compounds contemplated in this invention may be applied as insecticides, nematocides and miticides according to methods known to those skilled in the art. Pesticidal compositions usually comprise a carrier and/or diluent, either liquid or solid. Suitable liquid diluents or carriers include water, petroleum distillates or other liquid carriers with or without surface active agents. Useful solid carriers include clay, talc, bentonite, diatomaceous earth, fullers earth and the like.

Pesticidal compositions containing the compounds of this invention as the active toxicant may be used in the form of liquid concentrates or as powder, granular formulations, or other solid formulations. However, because of the unique water solubility characteristics of many of the compounds of this invention, either the technical materials or any appropriate formulation may be dissolved directly in water in sufficient amounts to attain the desired concentration levels. The water solution may then be applied to the pest by any conventional method known to those skilled in the art.

The required amount of the toxicants contemplated herein may be applied per acre treated in from 1 to 200 gallons or more of liquid carrier and/or diluent or in from about 5 to 500 pounds of inert solid carrier and/or diluent. The concentration in solid formulations may vary from about 0.5 to about 100 percent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied, and they have relatively high residual toxicity coupled with reduced levels of peroral mammalian toxicity. With respect to plants, they have a high margin of safety in that when used in sufficient amount to kill or repel the insects, they do not burn or injure the plant, and they resist weathering which includes decomposition by ultra-violet light, oxidation, or hydrolysis in the presence of moisture or, at least such decomposition oxidation and hydrolysis as would materially decrease the desirable pesticidal characteristic of the toxicants or impart undesirable characteristics, for instance, phytotoxicity, to the toxicants. The toxicants are so chemically inert that they are compatible with substantially any other constituents of the spray schedule, and they may be used in the soil, upon the seeds, or the roots of plants without injuring either the seeds or rotts of plants. Mixtures of the active compound of this invention may be employed as well as combinations of the active compounds of this invention with other biologically active compounds.

What is claimed is:

1. A compound of the formula:

$$\left[ R_1OC(=O)-N(R_2)-C(=O)-Q^{2+}-C(=O)-N(R'_2)-COR'_1 \right]_n 2X^{-n}$$

wherein:
n is 1, 2 or 3;
$R_1$ and $R'_1$ are the same or different and are benzofuranyl, benzodioxanyl, benzothienyl, 1-naphthyl, dihydrobenzothienyl, 1-tetrahydronaphthyl, benzodioxanyl or dihydrobenzofuranyl all of which may be either unsubstituted or substituted with one or more alkyl groups having from 1 to 8 carbon atoms;
$R_2$ and $R'_2$ are the same or different and are alkyl having from 1 to 8 carbon atoms;
X is a quaternising anion selected from the group consisting of mono-valent, divalent or trivalent inorganic or organic anion whose charge equal n;
$Q^{2+}$ is an organic radical which contains two quaternary nitrogen moieties selected from the group consisting of:

$$-A-{}^+N(R_3)(R_4)-B-{}^+N(R'_3)(R'_4)-A'-,$$

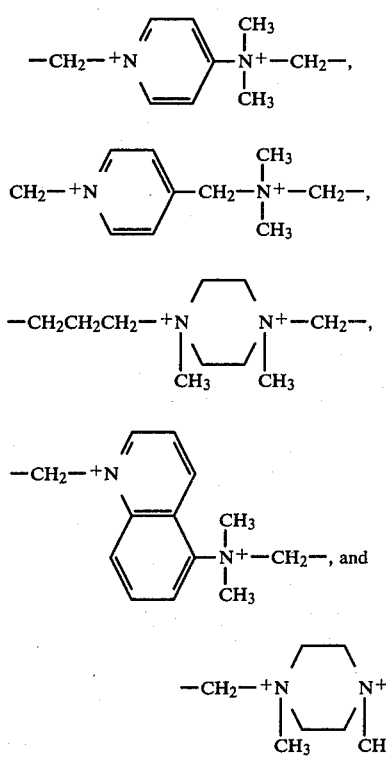

wherein:
- A and A' are the same or different and are divalent straight or branch chain alkylene or alkenylene having from 1 to 25 carbon atons;
- B is a divalent straight or branched chain alkylene or alkenylene which may include one divalent oxygen, sulfur, sulfinyl, sulfonyl, carbonyl or carbonyloxy group;
- $R_3$, $R'_3$, $R_4$ and $R'_4$ are:
  (a) individually, either substituted or unsubstituted alkyl, alkenyl or alkynyl; or
  (b) when $R_3$ and $R'_3$ are the same or different and are methyl or ethyl, $R_4$ and $R'_4$ are the same or different and are either a substituted or unsubstituted phenyl, naphthyl, cycloalkyl, or cycloalkenyl;

wherein the permissible substituents are one or more alkoxy, alkanoyloxy, alkoxycarbonyl, cyano, halo, nitro dialkylamino or alkanoyl groups.

2. A compound according to claim 1 wherein B is a linear or branched alkylene chain having from 1 to 25 carbon atoms which may include one divalent oxygen.

3. A compound according to claim 1 wherein:
$R_3$, $R'_3$, $R_4$ and $R'_4$ are the same or different and are alkyl, alkoxyalkyl, alkenyl or alkynyl all of which may be either unsubstituted or substituted with one or more alkanoyloxy, alkoxy, alkoxycarbonyl, alkanoyl or dialkylamino groups.

4. A compound according to claim 1 wherein X is chloride, bromide, fluoride, nitrate, iodide, bicarbonate, carbonate, sulfate, phosphate, acetate, propionate, lactate, formate, succinate, maleate, tartrate, citrate, p-toluenesulfonate, bensenesulfonate or methanesulfonate.

5. Compound according to claim 1 wherein X is chloride or lactate.

6. A compound according to claim 1 wherein $R_1$ and $R'_1$ is benzodioxolanyl or dihydrobenzofuranyl either unsubstituted or substituted with one or more alkyl groups.

7. A compound according to claim 1 wherein $R_1$ and $R'_1$ are 2,3-dihydro-2,2-dimethyl-7-benzofuranyl.

8. A compound according to claim 1 wherein R and R' are 2,2-dimethyl-4-benzo-1,3-dioxolanyl.

9. A compound according to claim 1 wherein $R_1$ and $R'_1$ are 1-naphthyl.

10. A compound according to claim 1 wherein $R_2$ and $R'_2$ are methyl.

11. A compound of the formula:

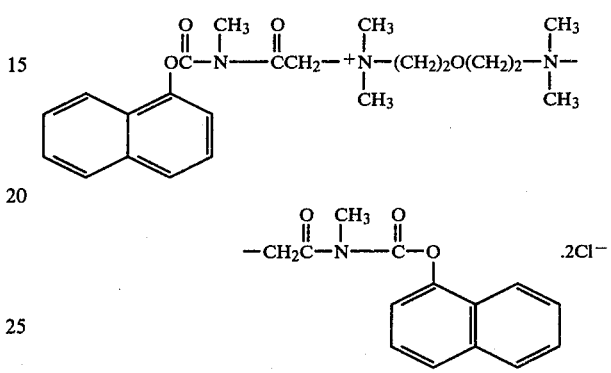

12. An insecticidal and miticidal composition comprising an acceptable carrier and as the active toxicant an insecticidally or miticidally effective amount of a compound to claim 2.

13. An insecticidal and miticidal composition comprising an acceptable carrier and as the active toxicant an insecticidally or miticidally effective amount of a compound according to claim 3.

14. An insecticidal and miticidal composition comprising an acceptable carrier and as the active toxicant an insecticidally or miticidally effective amount of a compound according to claim 4.

15. An insecticidal and miticidal composition comprising an acceptable carrier and as the active toxicant an insecticidally or miticidally effective amount of a compound according to claim 5.

16. An insecticidal and miticidal composition comprising an acceptable carrier and as the active toxicant an insecticidally or miticidally effective amount of a compound according to claim 6.

17. An insecticidal and miticidal composition comprising an acceptable carrier and as the acitve toxicant an insecticidally or miticidally effect amount of a compound according to claim 7.

18. An insecticidal and miticidal composition comprising an acceptable carrier and as the active toxicant an insecticidally or miticidally effective amount of a compound according to claim 8.

19. An insecticidal and miticidal composition comprising an acceptable carrier and as the active toxicant an insecticidally or miticidally effective amount of a compound according to claim 9.

20. An insecticidal and miticidal composition comprising an acceptable carrier and as the active toxicant an insecticidally or miticidally effective amount of a compound according to claim 10.

21. An insecticidal and miticidal composition comprising an acceptable carrier and as the active toxicant an insecticidally or miticidally effective amount of a compound according to claim 11.

22. A method of controlling insects and mites which comprises subjecting them to an insecticidally or miticidally effective amount of a compound according to claim 3.

23. A method of controlling insects and mites which comprises subjecting them to an insecticidally or miticidally effective amount of a compound according to claim 4.

24. A method of controlling insects and mites which comprises subjecting them to an insecticidally or miticidally effective amount of a compound according to claim 5.

25. A method of controlling insects and mites which comprises subjecting them to an insecticidally or miticidally effective amount of a compound according to claim 6.

26. A method of controlling insects and mites which comprises subjecting them to an insecticidally or miticidally effective amount of a compound according to claim 7.

27. A method of controlling insects and mites which comprises subjecting them to an insecticidally or miticidally effective amount of a compound according to claim 8.

28. A method of controlling insects and mites which comprises subjecting them to an insecticidally or miticidally effective amount of a compound according to claim 9.

29. A method of controlling insects and mites which comprises subjecting them to an insecticidally and miticidally effective amount of a compound according to claim 10.

30. A method of controlling insects and mites which comprises subjecting them to an insecticidally and miticidally effective amount of a compound according to claim 11.

31. A compound of the formula:

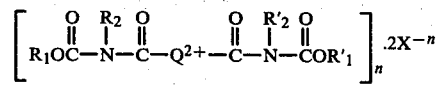

n is 1, 2 or 3;

$R_1$ and $R'_1$ are the same or different and are individually 1-naphthyl or 1-tetrahydronaphthyl all of which may be eight unsubstituted or substituted with one or more alkyl groups having from 1 to 8 carbon atoms;

$R_2$ and $R'_2$ are the same or different and are alkyl having from 1 to eight carbon atoms;

X is a quaternising anion selected from the group consisting of mono-valent, divalent or trivalent inorganic or organic anions whose charge equals n;

$Q^+$ is an organic radical of the formula:

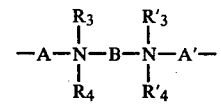

wherein:
A and A' are the same or different and are linear or branched alkylene or alkenylene chains having from 1 to 25 carbon atoms;
B is a linear or branched alkylene chain having from 1 to 25 carbon atoms which may include one divalent oxygen, sulfur, sulfinyl, sulfonyl, carbonyl or carbonyloxy group;
$R_3$, $R'_3$, $R_4$ and $R'_4$ are individually either substituted or unsubstituted alkyl, alkenyl or alkynyl wherein the permissible substituents are alkoxy, alkanoyloxy, alkoxycarbonyl, cyano, halo, nitro, dialkylamino or alkanoyl.

32. A compound according to claim 31 wherein X is chloride, bromide, fluoride, nitrate, iodide, bicarbonate, carbonate, sulfate, phosphate, acetate, propionate, lactate, formate, succinate, maleate, tartrate citrate p-toluenesulfonate, benzensulfonate or methanesulfonate.

33. A compound according to claim 31 wherein B is divalent alkylene, alkyloxyalkyl, alkylthioalkyl, alkylsulfinylalkyl, alkylsulfonylalkyl, or alkyloxycarboxyl alkyl, alkylcarbonylalkyl.

34. An insecticidal and miticidal composition comprising an acceptable carrier and as the active toxicant an insecticidally or miticidally effective amount of a compound according to claim 31.

35. An insecticidal and miticidal composition comprising an acceptable carrier and as the active toxicant an insecticidally or miticidally effective amount of a compound according to claim 32.

36. An insecticidal and miticidal composition comprising an acceptable carrier and as the active toxicant an insecticidally or miticidally effective amount of a compound according to claim 33.

37. A method of controlling insects and mites which comprises subjecting them to an insecticidally and miticidally effective amount of a compound according to claim 31.

38. A method of controlling insects and mites which comprises subjecting them to an insecticidally or miticidally effective amount of a compound according to claim 32.

39. A method of controlling insects and mites which comprises subjecting them to an insecticidally or miticidally effective amount of a compound according to claim 33.

40. A compound according to claim 1 wherein $Q^{2+}$ is

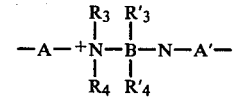

* * * * *

UNITED STATES PATENT AND TRADEMARK OFFICE
CERTIFICATE OF CORRECTION

PATENT NO. : 4,430,341
DATED : February 7, 1984
INVENTOR(S) : BARBARA W. KAPLAN

It is certified that error appears in the above-identified patent and that said Letters Patent is hereby corrected as shown below:

Column 8: line 43: insert

--

METHOD II

A. 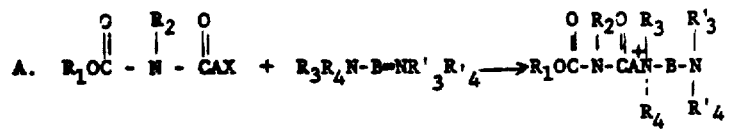

B. 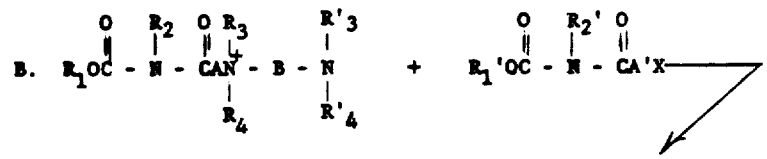

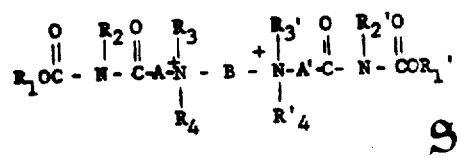

--

Signed and Sealed this

Twentieth Day of November 1984

[SEAL]

Attest:

GERALD J. MOSSINGHOFF

Attesting Officer    Commissioner of Patents and Trademarks